United States Patent [19]

VandenBerg

[11] Patent Number: Plant 7,211

[45] Date of Patent: Apr. 3, 1990

[54] CHRYSANTHEMUM PLANT NAMED CARTAGO

[75] Inventor: Cornelis P. VandenBerg, Salinas, Calif.

[73] Assignee: Yoder Brothers, Inc., Barberton, Ohio

[21] Appl. No.: 337,461

[22] Filed: Apr. 13, 1989

[51] Int. Cl.[4] ..... A01H 5/00

[52] U.S. Cl. ..... Plt./74

[58] Field of Search ..... Plt./74

*Primary Examiner*—James R. Feyrer

*Attorney, Agent, or Firm*—Foley & Lardner, Schwartz, Jeffery, Schwaab, Mack, Blumenthal & Evans

[57] ABSTRACT

A Chrysanthemum plant named Cartago particularly characterized by its flat capitulum form; daisy capitulum type; yellow ray floret color; diameter across face of capitulum of up to 7 cm at maturity when grown as a pinched spray pot mum; uniform eight week photoperiodic flowering response to short days; short plant height when grown as a pinched pot mum; and spreading branching pattern.

3 Drawing Sheets

The present invention comprises a new and distinct cultivar of Chrysanthemum, botanically known as *Dendranthema grandiflora,* and referred to by the cultivar name Cartago.

Cartago, identified as 83-A0107, was originated from a cross made by Cornelis P. VandenBerg in a controlled breeding program in Salinas, Calif., in 1983.

The female parent of Cartago was an unnamed seedling identified as 79-F53001. The male parent of Cartago was an unnamed seedling identified as 79-U33028.

Cartago was discovered and selected as one flowering plant within the progeny of the stated cross by Cornelis P. VandenBerg in May of 1984, in a controlled environment in Salinas, Calif.

The first act of asexual reproduction of Cartago was accomplished when vegetative cuttings were taken from the initial selection in July of 1984 in a controlled environment in Salinas, Calif., by technicians working under formulations established and supervised by Cornelis P. VandenBerg.

Horticultural examination of controlled flowerings of successive plantings has shown that the unique combination of characteristics as herein disclosed for Cartago are firmly fixed and are retained through successive generations of asexual reproduction.

Cartago has not been observed under all possible environmental conditions. The phenotype may vary significantly with variations in environment such as temperature, light intensity and daylength.

The following observations, measurements and comparisons describe plants grown in Salinas, Calif. and Leamington, Canada, under greenhouse conditions which approximate those generally used in commercial greenhouse practice.

The following traits have been repeatedly observed and are determined to be basic characteristics of Cartago, which, in combination, distinguish this Chrysanthemum as a new and distinct cultivar:

1. Flat capitulum form.
2. Daisy capitulum type.
3. Yellow ray floret color.
4. Diameter across face of capitulum up to 7 cm at maturity, when grown as a pinched spray pot mum.
5. Uniform eight week photoperiodic flowering response to short days.
6. Short plant height, requiring 7 to 14 long days after pinch prior to short days and 0 to 1 application of 2500 ppm B-9 SP to attain a flowered plant height of 25 to 35 cm for year-round flowerings when grown as a pinched pot mum in a 15 cm pot.
7. Branching pattern is spreading.

The accompanying photographic drawings show typical inflorescence and leaf characteristics of Cartago, with the colors being as nearly true as possible with illustrations of this type.

Sheet 1 is a color photograph of Cartago grown as a pinched spray pot mum grown in a 10 cm pot.

Sheet 2 is a black and white photograph of three views of the inflorescence of Cartago.

Sheet 3 is a black and white photograph showing the upper and under sides of the leaves of Cartago at three stages of development (mature, intermediate and immature).

Of the commercial cultivars known to the inventor, the most similar in comparison to Cartago is Pert, disclosed in U.S. Plant Pat. No. 4,764. Reference is made to attached Chart A, which compares certain characteristics of Cartago to the same characteristics of Pert.

Similar traits are ray floret color, capitulum form and type, branching pattern, plant height and flowering response. Cartago has a smaller diameter across face of capitulum than Pert. In addition, flower placement of Cartago is more open and attractive than that of Pert, which often is clubby and with angled flowers.

In the following description color references are made to The Royal Horticultural Society Colour Chart. The color values were determined on plant material grown as a pinched spray pot mum in Salinas, Calif. on Oct. 14, 1988.

Classification:

*Botanical.*—*Dendranthema grandiflora* cv. Cartago.

*Commercial.*—Daisy spray pot mum.

INFLORESCENCE

A. Capitulum:

*Form.*—Flat.

*Type.*—Daisy.

*Diameter across face.*—Up to 7 cm at maturity.

B. Corolla of ray florets:

*Color (general tonality from a distance of three meters).*—Yellow.

*Color (upper surface).*—5A.
*Color (under surface).*—5B.
*Shape.*—Straight, concave.

C. Corolla of disc florets:
*Color (mature).*—9A.
*Color (immature).*—144B to 144C.

D. Reproductive organs:
*Androecium.*—Present on disc florets only; no pollen.
*Gynoecium.*—Present on both ray and disc florets.

PLANT

A. General appearance:
*Height.*—Short; 25 to 35 cm as a pinched spray pot mum with 7 to 14 long days after pinch prior to short days and 1 application of 2500 ppm B-9 SP.
*Branching pattern.*—Spreading.

B. Foliage:
*Color (upper surface).*—147A.

*Color (under surface).*—147B.
*Shape.* —Lobed and slightly serrated.

CHART A

COMPARISON OF CARTAGO AND PERT

| Cultivar | Cartago | Pert |
|---|---|---|
| Ray Floret Color | Yellow | Yellow |
| Capitulum Form and Type | Flat Daisy | Flat Daisy |
| Branching Pattern | Spreading | Spreading |
| Diameter Across Face of Capitulum | Up to 7 cm | 70 to 90 mm |
| Plant Height | Short | Short |
| Controlled Response | 8 Weeks | 8 Weeks |

Comparisons Made Of Plants Grown As Pinched Spray Pot Mums In Salinas, California

I claim:

1. A new and distinct Chrysanthemum plant named Cartago, as described and illustrated.

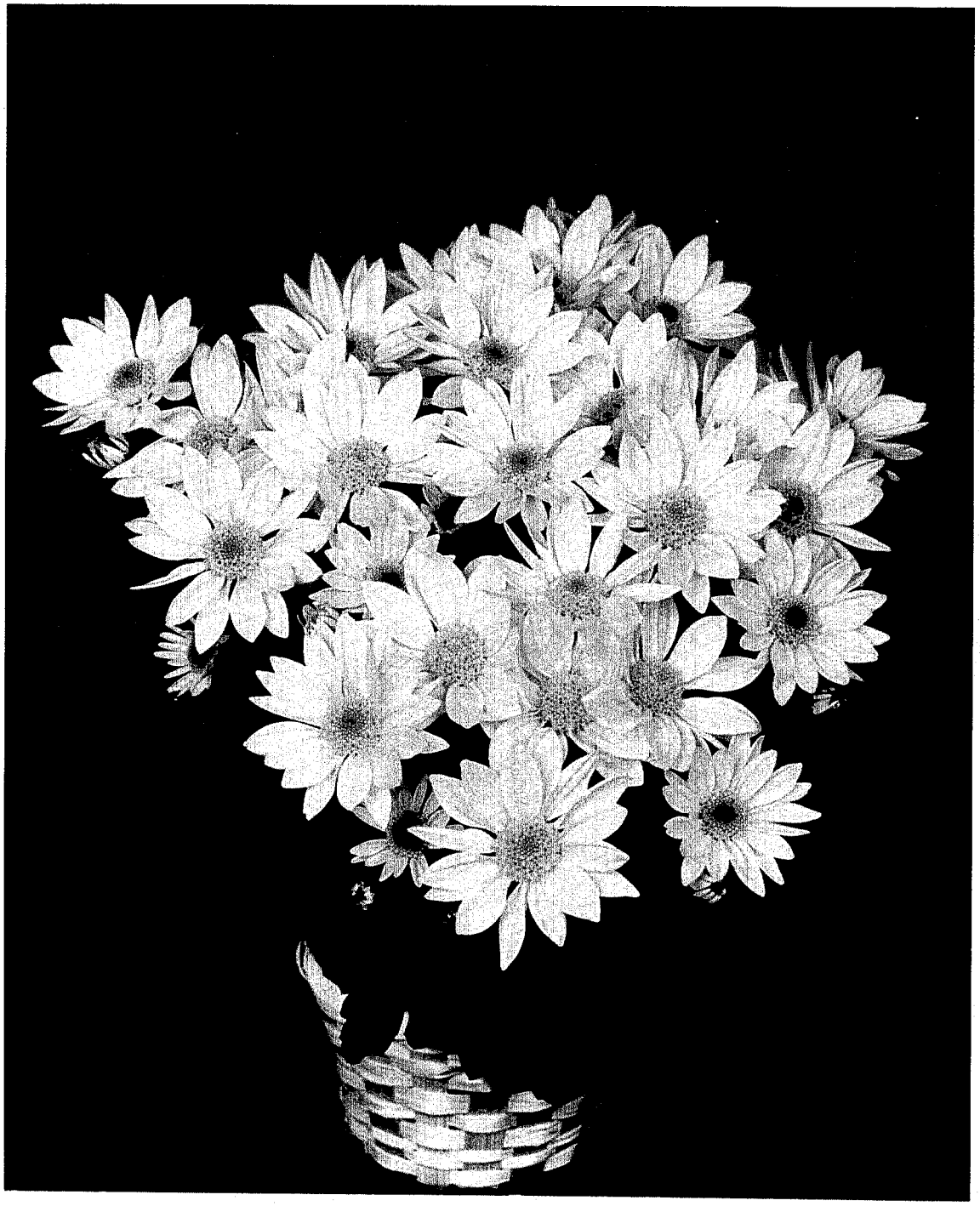

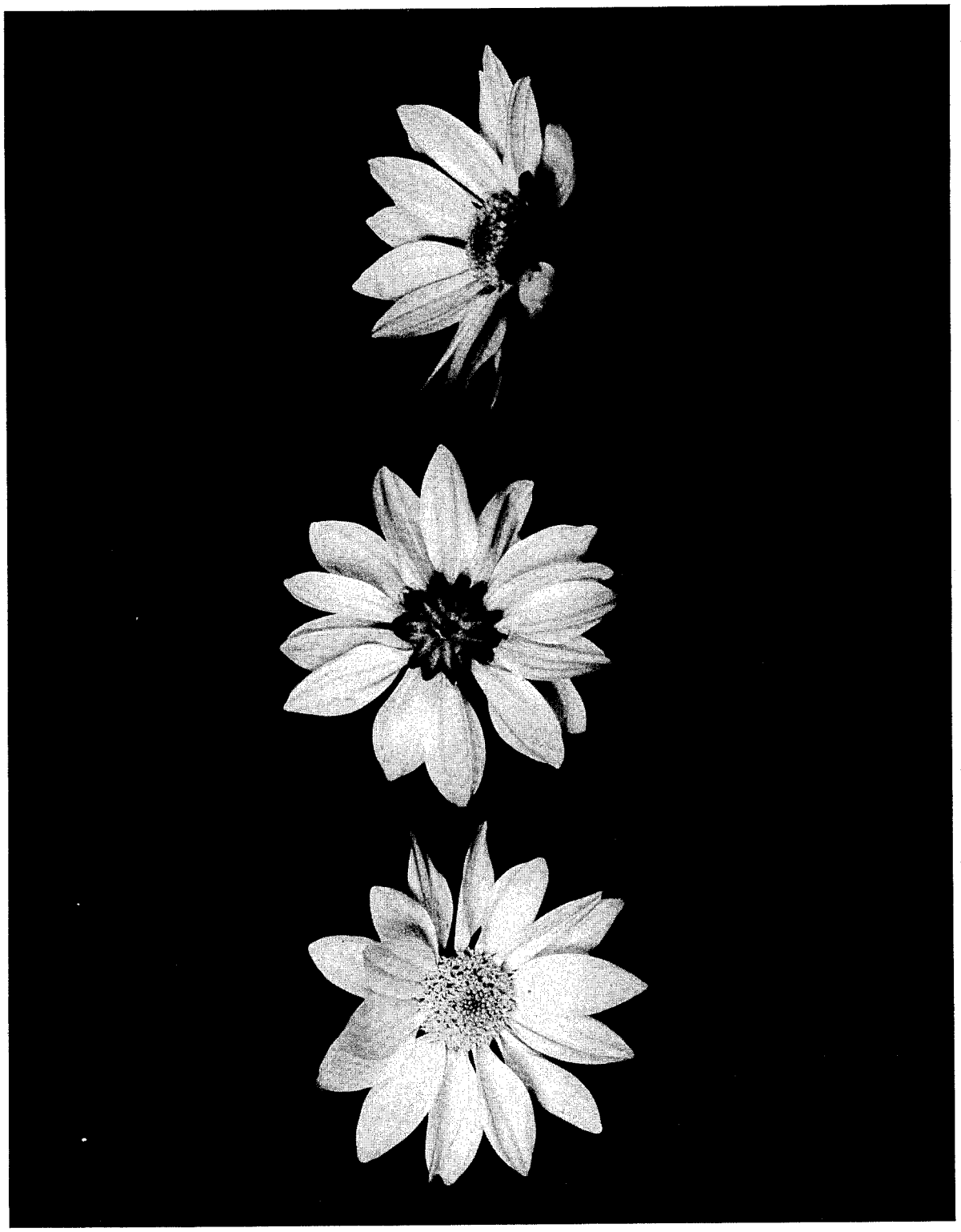

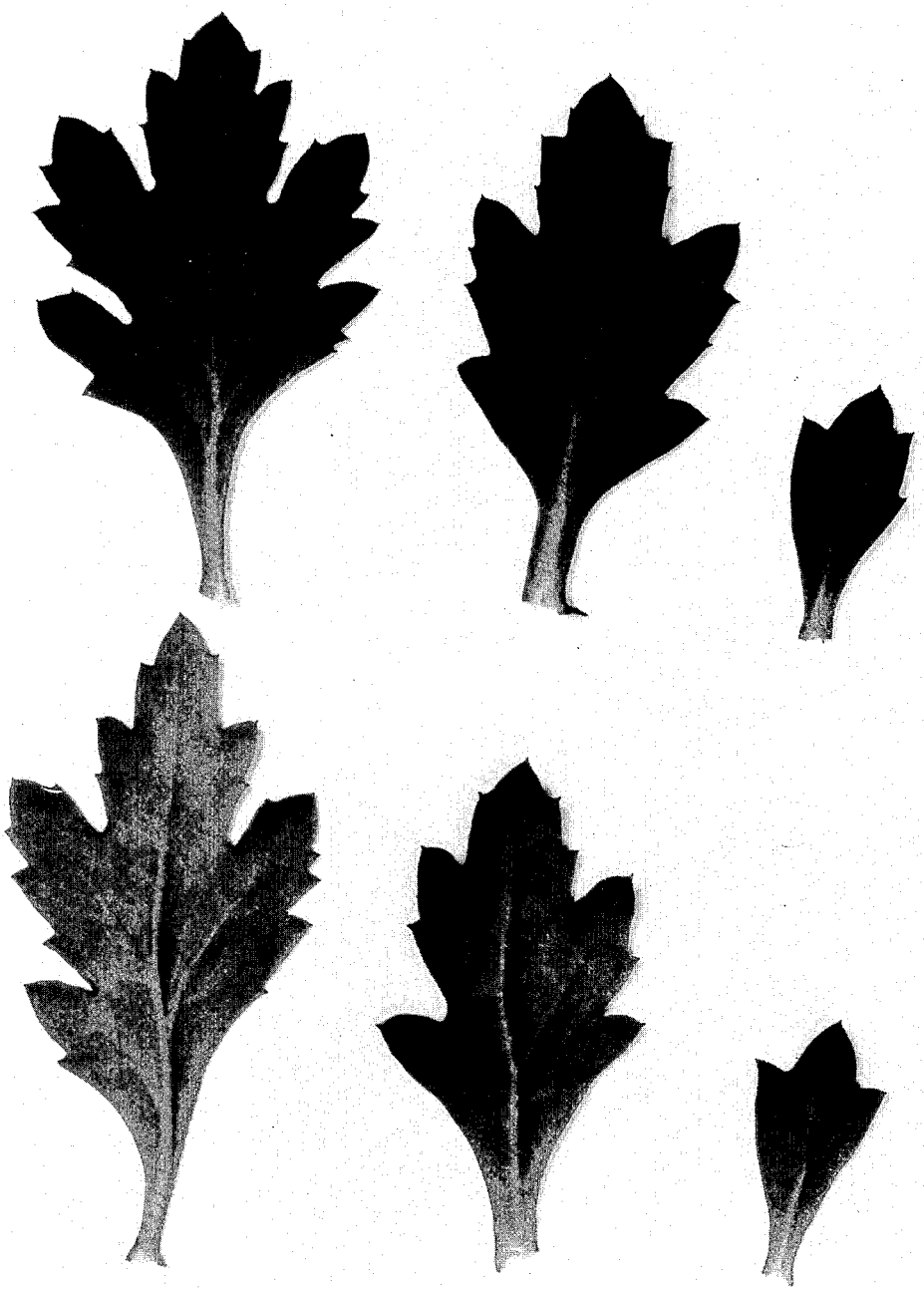

* * * * *